United States Patent [19]

Gittleman

[11] 4,359,318
[45] Nov. 16, 1982

[54] DENTAL IMPLANT

[76] Inventor: Neal Gittleman, 4039 Spruce St., Philadelphia, Pa. 19104

[21] Appl. No.: 332,159

[22] Filed: Dec. 18, 1981

[51] Int. Cl.³ .................................................. A61C 8/00
[52] U.S. Cl. .................................................. 433/173
[58] Field of Search ................................. 433/173, 175

[56] References Cited

U.S. PATENT DOCUMENTS 4,027,393 6/1977 Ellis et al. ............................ 433/173
4,180,910 1/1980 Straumann ........................... 433/173

Primary Examiner—Robert Peshock
Attorney, Agent, or Firm—Lerner, David, Littenberg & Samuel

[57] ABSTRACT

A dental implant system, including a novel dental implant is disclosed, along with a method of installing the same. The implant includes a sleeve member with a cylindrical bottom portion including a plurality of aperturess and a neck portion. An electrically non-conductive collar member is mounted within the neck portion and an electrode is mounted within the collar portion electrically isolated from the sleeve member. The top portion of the electrode is adapted to be releasably electrically connected with a battery pack and alternatively with a dental appliance. The battery pack includes a battery whose cathode connects with a member which engages the top portion of the electrode and an anode which makes contact with the inside of the mouth. An appliance for preparing the jaw bone for the insertion of the implant is also disclosed, including a drill with three cutting surfaces and a jig adapted to support the drill within the mouth. After installation of the implants, use of the battery pack causes bone apposition through the apertures in the sleeve member to form an extremely solid mechanical interlock. The battery pack may be replaced with a dental appliance after the bone is formed.

19 Claims, 8 Drawing Figures

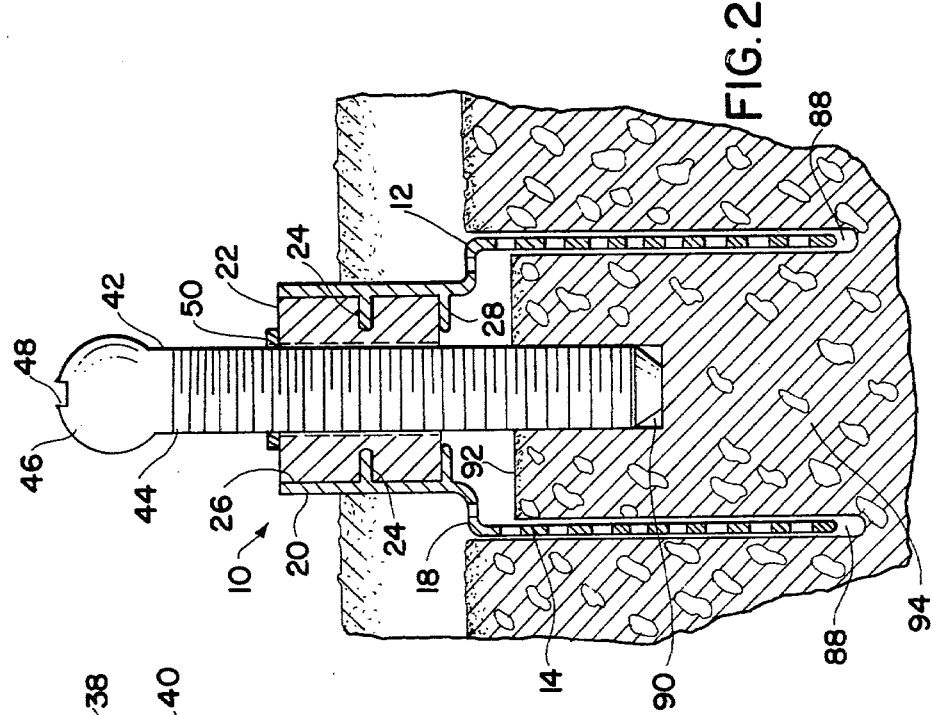
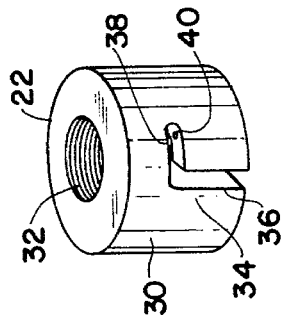
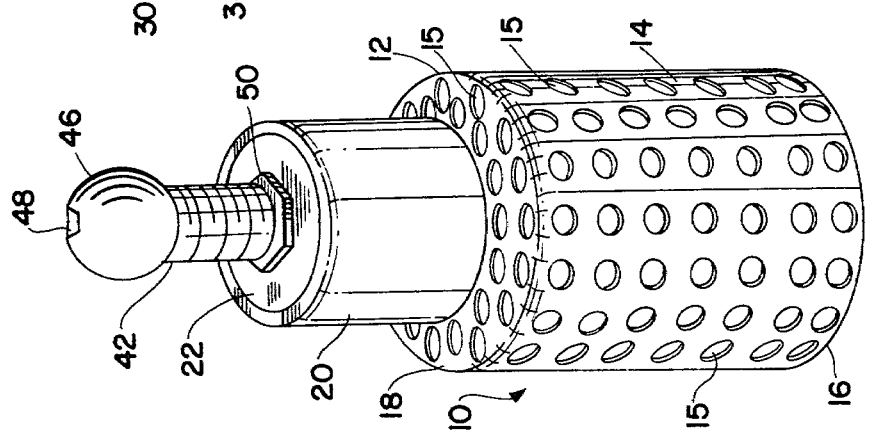

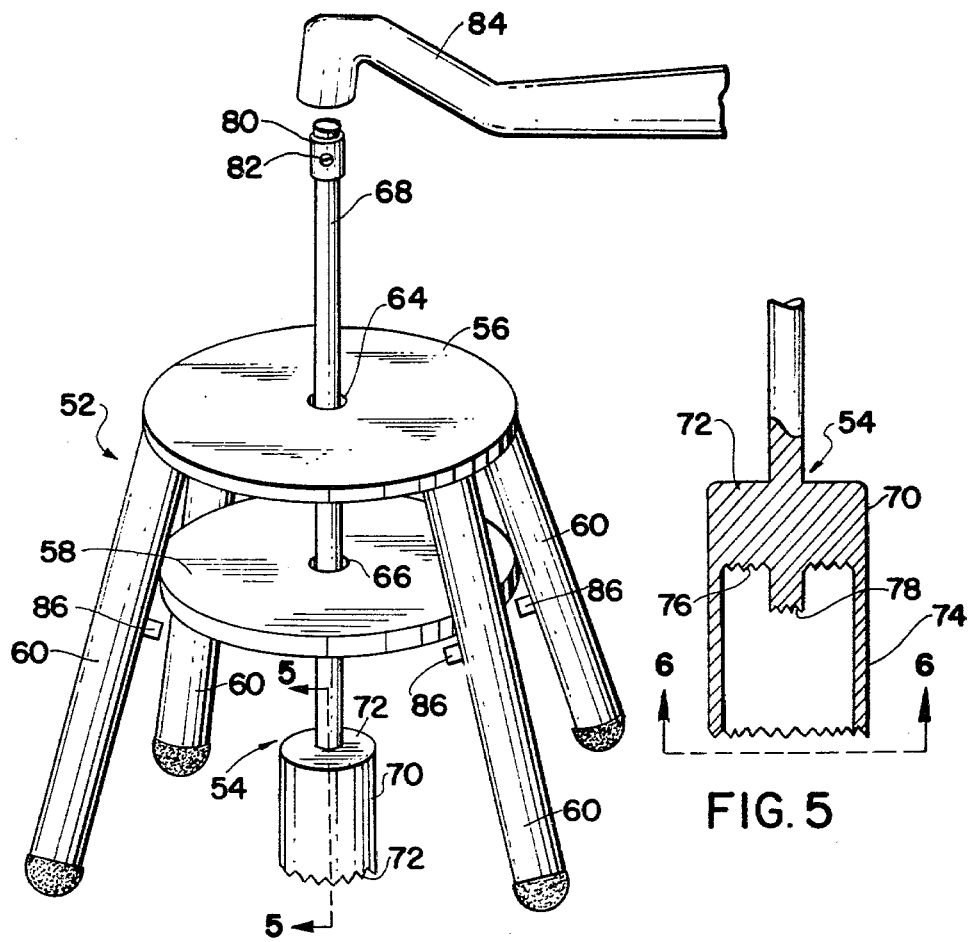
FIG. 4
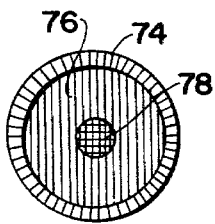
FIG. 5
FIG. 6

DENTAL IMPLANT

FIELD OF THE INVENTION

This invention relates to a new and improved dental implant, a method of preparing such implant and an apparatus utilized in conjunction therewith.

BACKGROUND OF THE INVENTION

For a dental implant to be effective, it must form as solid a bond as possible with the jaw in as short a period as possible. Numerous dental implant systems have been suggested over the years for attaching false teeth and other dental appliances to the jaw. A number of approaches have included the use of an implant having an open or cage-like structure with holes or apertures which take advantage of bone growth through the apertures during the healing stage. Such approaches are illustrated in U.S. Pat. No. 1,216,683 in the name of E. J. Greenfield and U.S. Pat. No. 4,180,910 in the name of Fritz Straumann, et al. In such devices, the implant has apertures or interstices through which bone may knit subsequent to the insertion of the implant into the jaw thus in order to more firmly anchor the dental appliance. Other implant arrangements which provide openings to receive bone growth include those shown in U.S. Pat. No. 3,979,828 in the name of Bill E. Taylor and U.S. Pat. No. 3,576,074 in the name of Sidney D. Gault, et al.

These implants have generally provided little anchoring power until such time as the bone has had an opportunity to grow, thus rendering it possible for the implant to loosen while the bone is knitting.

It is also known that electricity stimulates bone growth, including bone growth in the human jaw. For example, U.S. Pat. No. 4,027,392 in the name of Philip M. Sawyer et al. discloses an implant embedded in bone and a battery which supplies D.C. current to aid in the formation of bone. Although the use of electricity to encourage bone growth has been recognized, a truly effective implant which utilizes this concept in the formation of a permanent and solidly anchored implant has yet to be devised.

A further problem with dental implants is that there is always a risk of infection. It is known, as illustrated in U.S. Pat. No. 4,252,525 in the name of Frank W. Child, that electricity is helpful in inhibiting infection. However, such approaches have failed to recognize that the electricity which can be utilized to inhibit infection can simultaneously be utilized to promote bone growth during the healing.

Accordingly, it is an object of the present invention to provide an improved dental implant.

It is a further object of the present invention to provide an improved dental implant which is permanently anchored in the jaw through bone growth.

It is another object of the present invention to provide such an implant which restricts movement in a mesial-distal direction and a buccal-lingual direction.

It is still another object of the present invention to provide such an improved implant which is firmly anchored to the jaw during the period of healing and bone growth.

It is still another object of the invention to provide a dental implant which achieves maximum anchoring strength more rapidly than would be accomplished through natural bone growth.

It is yet another object of the present invention to provide such a dental implant which avoids inflammation, infection and hard tissue resorption.

It is still a further object of the present invention to provide a complete implant system including an implant and a power supply, along with a dental appliance which can be anchored to the implant.

It is still a further object of the present invention to provide a method for forming and inserting such an improved dental implant.

It is still another object of the present invention to provide an apparatus for preparing the jaw bone for the insertion of such improved dental implant.

Various other objects and advantages of the present invention will become clear from the following detailed description of several exemplary embodiments thereof, and the novel features will be particularly pointed out in conjunction with the claims appended thereto.

SUMMARY OF THE INVENTION

In accordance with the teachings of the present invention, an implant for attaching a dental appliance to a jaw bone comprises a sleeve member having a substantially cylindrical vertically extending bottom portion including a plurality of apertures therethrough, an open bottom, and a cylindrical neck portion positioned above said bottom portion. The bottom portion is constructed and arranged to be snugly inserted into an annular cut formed in the upper surface of the jaw bone to there define an upwardly extending substantially cylindrical stump. An electrically nonconductive collar member is mounted within the neck portion of the sleeve member and has a central vertically extending opening. An electrode means is mounted to the collar member within the central opening and is electrically isolated from the sleeve member. The electrode means has an upwardly extending top portion adapted to be releasably electrically connected with a source of electricity and to receive electricity therefrom and to also releasably retain a dental appliance. A downwardly extending bottom portion is constructed and arranged to make electrical contact with the stump.

A complete dental implant system in accordance with the present invention comprises an implant of the aforesaid type along with a power supply member adapted to be mounted to the top portion of the electrode. The power supply member includes at least one mating member adapted to receive and releasably grasp and make electrical contact with the electrode. At least one battery is electrically connected to the mating member to supply electrical current to the mating member, whereby electricity may be transferred to the electrode means when the implant and the electrical member are engaged.

A method of forming or installing such a dental implant comprises the steps of forming an annular cut in the top surface of the jaw bone to define an upwardly extending substantially cylindrical stump and forming a downwardly extending central opening within the stump. An implant of the type previously described is inserted so that the bottom portion of the sleeve member is inserted into the annular cut and the bottom portion of the electrode is in contact with the central opening of the stump. An electrical current is applied to the top portion of the electrode so that the electrode conducts electricity to the stump to cause bone apposition in the stump, so that bone tissue knits through the apertures in the sleeve member.

The present invention will be more fully understood by reference to the following detailed description of several exemplary embodiments thereof in conjunction with the accompanying drawings in which:

FIG. 1 is an isometric view of the implant of the present invention;

FIG. 2 is a cross sectional view of an implant of the type shown in FIG. 1 after it has been inserted into the jaw bone;

FIG. 3 is an isometric view of the collar member of the present invention;

FIG. 4 is an isometric view of the apparatus for preparing the jaw bone for the insertion of the dental implant, including the jig member, and illustrating how such apparatus may be interconnected with a standard dental drill;

FIG. 5 is a partial sectional view of the cutting tool portion of the aforesaid apparatus taken along the line 5—5 in FIG. 4 and looking in the direction of the arrows;

FIG. 6 is a bottom plan view of the aforesaid cutting portion taken along the line 6—6 in FIG. 7 and looking in the direction of the arrows;

DESCRIPTION OF THE PREFERRED EMBODIMENT

Figures 7, 8:
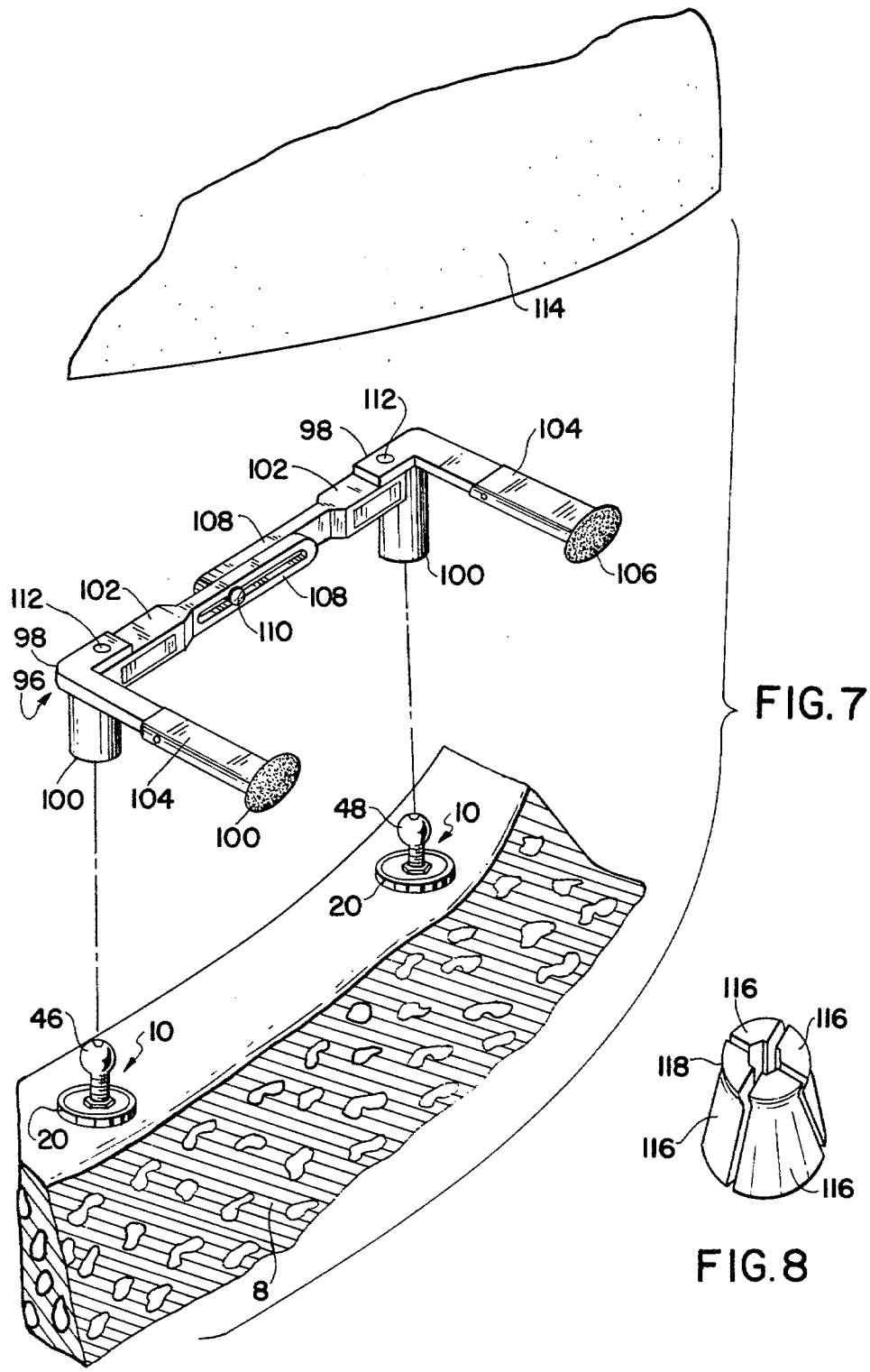
FIG. 7 is an isometric view showing a cutaway portion of a jaw bone in which two implants of the present invention have been installed and illustrating schematically the relationship between said implants and the internal mechanisms of the power supply member.
FIG. 8 is an isometric view of an alternative embodiment of the top portion of the electrode means.

Referring now to the drawings, wherein like reference numerals designate like parts throughout the several views, and more particularly to FIGS. 1 and 2, there is shown a dental implant designated generally by reference numeral 10. The implant 10 has a sleeve member 12 which is preferably constructed from surgical titanium or alternatively a ceramic or possibly one of the hydroxylapatite ($Ca_{10}(PO_4)_6(OH)_2$) materials.

The sleeve member 12 includes a bottom portion 14 which is substantially cylindrical and extends vertically downward to form an open bottom 16. A shoulder portion 18 extends radially inward from the top of the bottom portion 14 of the sleeve member 12. A cylindrical neck portion 20 extends vertically upward from the inner edge of the shoulder portion 18 up to the top end of the sleeve member 12. A series of apertures or holes 15 are provided in the bottom portion 14 and the shoulder portion 18 of the sleeve member 12.

Means are provided in the neck portion 20 of the sleeve member 12 to securely retain the collar member 22 (which is discussed in more detail below). As seen in FIG. 2, a series of studs 24 extend inwardly from the inner surface 26 of the neck portion 20. There are preferably four such studs 24, which are spaced 90 degrees apart from one another. Additionally, a shelf 26 extends inwardly from the inner surface 26 of the neck 20. The shelf 28 is preferably continuous throughout the circumference of the neck portion 20, although it will be appreciated that this is not completely necessary and that a series of studs similar to the studs 24 might also suffice.

The collar member 22 is formed from an electrically nonconductive material which is preferably yieldable, such as a cross-linked polymer, to minimize the transmission of forces from the dental appliance to the bone and to provide yielding characteristics similar to the natural dentition. As is known to those skilled in the art, natural dentition has biomechanical toleration and dissipation of occlusional forces, so that teeth have limited movement and return to their original positions after being subjected to a force. Thus, as will become clearer below, the collar member 22 acts as an electrical insulator as well as an artificial periodental ligament.

The collar member 22, as seen in FIGS. 2 and 3, has a generally cylindrical shape with a smooth outer surface 30 and a threaded central vertically extending opening 32. The collar member 22 has four L-shaped grooves formed on its outside surface, each of which has a generally vertical portion 36 and a generally horizontal portion 38. A detent 40, in the form of a small protrusion, is positioned near the end of the horizontal portion 38.

The four L-shaped grooves 34 are spaced 90 degrees apart to correspond with the spacing of the studs 24. The depth of the grooves 34 must be sufficient to accomodate the studs 24; however it will be appreciated that the sleeve member 12 is to be electrically insulated from the electrode (to be discussed below), so that the grooves 34 should not be too deep to allow an accidental puncture of the collar member 22 by the studs 24. The radial length of the studs 24 (as well as the shelf 28) should also be carefully controlled so that there is no possibility of accidental electrical contact with the electrode.

The electrode 42 has a generally cylindrical shape with external threading 44 having a diameter and pitch to correspond the internal threading of the central opening 32 in the collar member 22. At the top portion of the electrode 42 there is provided a means to releasably electrically connect the electrode with a source of electricity so that the electrode receives electricity from that source. As shown in FIGS. 1 and 2, this is preferably accomplished with a Dalbo stud 46, which has a generally spherical solid shape and which engages with a slightly resilient female connector, as discussed below. The Dalbo stud 46 has a hexagonal opening 48 at the top thereof to receive a hexagonal or Allen wrench to allow the electrode to be screwed into the bone.

The implant 10 is also provided with a hexagonal nut 50 which is internally threaded so that it can be screwed on to the electrode 42 and be tightened against the collar member 22. It will be appreciated that the outer diameter of the nut 50 should not be so great that it comes into electrical contact with the neck portion 20 of the sleeve member 12.

The assembly of the implant 10 will now be described. As previously indicated, the sleeve member 12 is preferably a single unitary structure including the bottom portion 14, the shoulder portion 18, the neck portion 20, the studs 24 and the shelf 28. The collar member 22 is inserted downwardly into the neck portion 20 so that the studs 24 pass through the vertical portions 36 of the L-shaped grooves 34. The collar member 22 continues its downward travel until the bottom of the collar 22 reaches the shelf 28. In this position, the studs 24 are aligned with the horizontal portions 38 of the grooves 34. The collar 22 is then turned clockwise within the neck portion 20 so that the studs travel throught the horizontal portions 38 until they are locked in by the detent 40.

Prior to inserting the electrode 42, the nut 50 is screwed on the outer surface of the electrode 42 up to a location close to the Dalbo stud 46. The electrode is then screwed into the collar member 22 until it projects downwardly into the cavity formed by the bottom portion 14 of the sleeve member 12.

In order to fully explain how the jaw bone is prepared for receiving the implant 10 of the present invention, it is necessary to consider the apparatus used therefore, which is an additional aspect of the present invention. As shown in FIG. 4, a jig 52 is provided to support a drill 54. The jig 52 has an upper circular plate 56, a lower circular plate 58 and four legs 60. At the bottom of each leg 60 is a retaining device capable of securing acrylic which is adapted to study models prior to surgery to ensure an accurate positioning of the annular cut. Holes 64, 66 are provided in the upper and lower circular plates 56, 58 respectively to receive the shaft 68 of the drill 54. The jig 52 also includes a series of nozzles 86 for spraying a cooling stream onto the drill while it is in operation. The jig 52 includes fluid passages and an inlet connection (not shown).

As best seen in FIG. 5, the drill 54 has a drilling end 70 with three different cutting surfaces. There is provided an axially extending circular member 72 which is mounted to the end of the shaft 68. A cylindrical cutting member 74 is mounted to the outer perimeter of the circular member 72 and extends longitudinally downward to form a circular cutting surface, which forms an annular cut when the drill 54 is operated.

In the interior of the cylindrical cutting member 74, on the internal surface of the axially extending circular member 72, is a shaving surface 76. The third cutting surface is a central drilling member 78 which is designed to bore a cylindrical hole more shallow than the annular groove formed by the cylindrical cutting member 74. At the top of the drill 54 is a sleeve 80 with a set screw 82 to provide for a connection with a standard contra-angled hand piece 84.

Returning now to FIG. 2, it will be appreciated that the drill 54 makes three different types of cuts in the jaw bone 8. Specifically, the cylindrical cutting member 74 forms an annular cut 88 which defines an upwardly extending stump 94. The central drilling member 78 forms a central opening 90 within the stump 94. The diameter of the central opening 90 should be slightly larger than the outer diameter of the threaded portion 44 of the electrode 42, so that the electrode 42 makes contact with the stump 94 at its bottom of central opening 90. The shaving surface 76 has the effect of shaving down and providing a lower top surface 92 in the stump 94.

To insert the implant 10 into the jaw bone after is has been prepared as just described, the assembled implant 10 is lowered into the jaw bone so that the bottom portion 14 of the sleeve member 12 enters the annular cut 88. The electrode 42 is inserted into the central opening 90 within the stump 94. Through the use of a hexagonal or Allen wrench applied to the hexagonal opening 48 at the top of the electrode 42, the electrode is guided into the central opening 90 and the end of the electrode 42 is thus in contact with the stump 94.

It will be appreciated by those skilled in the art that the details and dimensions of the implant 10 can be varied in numerous ways depending on the patient and other circumstances. It is believed that the annular cut 88 and thus the diameter of the bottom portion 14 should be approximately 8½ millimeters. The longitudinal length of the bottom portion 14 is approximately 9¼ millimeters. The shoulder portion 18 is approximately one millimeter wide and the neck portion 20 is approximately five millimeters long and has a diameter of approximately six millimeters.

Referring now to FIG. 7, there is shown schematically the power supply member or battery pack used with the implant 10 of the present invention. FIG. 7 illustrates a segment of the jaw bone 8 with two implants 10 of the present invention already having been installed. The internal mechanism of the battery pack, generally referred to by reference numeral 96, has two links 98, one for each of the implants 10 which are mounted on the upper or lower jaw. Each link 98 has a downwardly extending female Dalbo unit 100, which is adapted to releasably but firmly engage the Dalbo stud 46 on the implant 10. Eac link 98 has a battery compartment 102 which encases a battery. The cathode portion of the battery is connected to the interior walls of the female Dalbo unit 100, so that the electrical charge can be passed through the female Dalbo unit 100 to the male unit 46 of the implant 10. Each link 98 also has an anode member 104 which telescopes outwardly and terminates in contact pad 106. Each link also has a slide arm 108 and a pin 110 links the two slide arms 108, so that they can be pivoted or translated with respect to each other. Additionally, pivots 112 are provided to allow the anode units 104 to be angularly pivoted with respect to the female Dalbo unit 100.

The entire internal mechanism 96 is encased in acrylic material, shown schematically by reference numeral 114, except that the anode units 104 protrude from the acrylic material 114 so that they can make contact with the inside of the mouth. Additionally, the openings of the female Dalbo unit 100 are not encased with acrylic and they are exposed so that they can engage with the male Dalbo unit 46 of the implants 10.

The mechanism 96 can be and should be adjusted to the circumstances of the patient. In various cases, the spacing of two or more implants may vary and each patient's mouth, of course, has different dimensions. It should also be appreciated that more than two links 98 can be used, whereby a given link 98 may have two slide arms 108 coming off in different directions to connect with two different other links 98.

It will now be appreciated that, with the female Dalbo unit 100 properly aligned to coincide with the placement of the male Dalbo unit 46, the power supply member can be placed on the two (or more) implants. When this is done, and electrical connection is made between the battery and the implant 10. When the pads 106 are placed against the patient's cheek or another portion of the patient's mouth, a circuit is formed which allows electrical current to flow into the electrode 42 of the implant 10. Since the electrode is highly conductive, the electricity is transmitted into the stump 94, which causes bone apposition outwardly through the apertures 15 to mesh with the bone on the other side of the annular cut 88. The electricity also has the effect of preventing infection and inflammation.

It will be appreciated that the battery pack does not rest on and is not supported by tissues. Instead, the weight is supported by the implants 10, which weight is transmitted to the jawbone 8. This allows the tissues to relax while the battery pack is worn.

The growth of bone, which will proliferate due to the supply of electricity, will create an exceedingly strong mechanical interlock between the implant 10 and the jaw bone. It is anticipated that the patient will use the battery pack for substantial periods of time during the healing period. The bone growth can be monitored radiologically. When sufficient bone growth has occurred, the battery pack can be removed and the prosthesis or dental appliance can be worn. The appliance will have female Dalbo units substantially identical to those in the battery pack, which will anchor the appliance to the implants firmly but releasably. Portions of the dental appliance will make contact with and be supported by the soft tissue, with the implant serving primarily for retention.

There may be a period during which the patient will wear the battery pack at night to provide additional bone growth, and may begin to wear the dental appliance during the day. In due course, the use of the battery pack will probabaly become unnecessary and the patient can simply wear the prosthesis during the day, removing it only at night. However, if bone resorption should begin to occur at a later date, the battery pack can again be used to provide additional bone growth.

FIG. 8 illustrates an alternative embodiment of the top end of the electrode 42. Instead of a Dalbo unit, a Ceka stud unit is provided which has four 90 degree segments 116 which are normally spaced apart from one another. Each of the segments 116 has a large diameter upper portion 118. When a Ceka unit as shown in FIG. 8 is used on the implant, the battery pack and the dental appliance must, of course, having a mating female Ceka unit (not shown), which has no resilience and which has an inner-small diameter portion with a diameter slightly smaller than the larger diameter portion 118. When the units are engaged, the small diameter portion of the female unit snaps over the large diameter portion 118 by squeezing the segments 116 together, thus providing a strong and tight (albeit releasable) fit.

It will be appreciated that the implant 10 of the present invention provides an unusually strong bond with the jaw bone 8 once the bone has knit through the apertures 15. The implant is retained in place by the soft tissues (gums) being sutured around the implant. The shoulder portion 18, being under the tissue, prevents dislodgement.

It will also be understood that the resilient collar member 22 provides yielding characteristics similar to those found in normal, healthy teeth, which lessens the risk of fracture when sudden forces are experienced.

As will be readily apparent to those skilled in the art, the invention may be used in other specific form without departing its spirit or essential characteristics. The present embodiments are, therefore, to be considered as illustrative and not restrictive, the scope of the invention being indicated by the claims rather than the foregoing description, and all changes which come within the meaning and range of equivilents of the claims are therefore intended to be embraced therein.

What is claimed is:

1. An implant for attaching a dental appliance to a jaw bone comprising:
    (a) a sleeve member having a substantially cylindrical vertically extending bottom portion including a plurality of apertures therethrough, an open bottom, and a cylindrical neck portion positioned above said bottom portion, said bottom portion being constructed and arranged to be snugly inserted into an annular cut formed in the upper surface of the jaw bone to there define an upwardly extending substantially cylindrical stump;
    (b) an electrically non-conductive collar member mounted within said neck portion of said sleeve member and having a central vertically extending opening; and
    (c) electrode means mounted to said collar member within said central opening and electrically isolated from said sleeve member, said electrode means having an upwardly extending top portion adapted to be releasably electrically connected with a source of electricity and to receive electricity therefrom and to also releasably retain a dental appliance, and a downwardly extending bottom portion constructed and arranged to make electrical contact with said stump.

2. An implant according to claim 1 wherein a shoulder portion extends radially inward from the top of said bottom portion and said neck portion extends upward from said shoulder portion.

3. An implant according to claim 2 further comprising apertures in said shoulder portion.

4. An implant according to claim 1 wherein at least the lower portion of said electrode means is externally threaded.

5. An implant according to claim 4 wherein said central opening of said collar member is internally threaded and said electrode means is screwed into said central opening of said collar member.

6. An implant according to claim 1 wherein said collar member is resilient.

7. An implant according to claim 1 wherein said collar member is made from a cross-linked polymer.

8. An implant according to claim 1 further comprising means for applying torque to said electrode means to screw said electrode means into contact with said stump.

9. An implant according to claim 8 wherein said torque application means is a hexagonal opening in the top surface of said electrode means adapted to receive a hexagonal wrench.

10. An implant according to claim 1 wherein said top portion of said electrode means has a male configuration and is constructed and arranged to mate with a dental appliance or a female socket associated with a source of electrical current.

11. A dental implant system comprising an implant for attaching a dental appliance to a jaw bone including a sleeve member having a substantially cylindrical vertically extending bottom portion including a plurality of apertures therethrough, an open bottom, and a cylindrical neck portion positioned above said bottom portion, said bottom portion being constructed and arranged to be snugly inserted into an annular cut formed in the upper surface of the jaw bone to there define an upwardly extending substantially cylindrical stump, an electrically non-conductive collar member mounted within said neck portion of said sleeve member and having a central vertically extending opening, and electrode means mounted to said collar member within said central opening and electrically isolated from said sleeve member, said electrode means having an upwardly extending top portion adapted to be releasably electrically connected with a source of electricity and to receive electricity therefrom and to also releasably retain a dental appliance, and a downwardly extending bottom portion constructed and arranged to make electrical contact with said stump; and a power supply member adapted to be mounted to said top portion of said electrode including at least one mating member adapted to receive and releasably grasp and make electrical contact with said electrode, and at least one battery electrically connected to said mating member to supply electrical current to said mating member whereby electricity may be transferred to said electrode means when said implant and said power supply member are engaged.

12. A dental implant system according to claim 11 wherein said at least one socket is connected to the negative terminal of the battery.

13. A dental implant system according to claim 11 further comprising a dental appliance having at least one mating member adapted to engage said top portion of said electrode when said top portion of said electrode is not engaged with said power supply member.

14. A dental implant system according to claim 11 wherein said power supply member includes a link associated with each mating member, said links being adjustably connected to each other to provide for adjustable spacing of said mating members.

15. A method of forming a dental implant comprising the steps of:
  (a) forming an annular cut in the top surface of the jaw bone to define an upwardly extending substantially cylindrical stump;
  (b) forming a downwardly extending central opening within said stump;
  (c) inserting an implant into said annular cut and said central opening, said implant including a sleeve member having a substantially cylindrical downwardly extending bottom portion including a plurality of apertures therethrough, an open bottom, an electrically non-conductive collar member mounted within said neck portion of said sleeve member and having a central vertically extending opening, and electrode means mounted to said collar member within said central opening and electrically isolated from said sleeve member, said electrode means having an upwardly extending top portion adapted to be releasably electrically connected with a source of electricity and to receive electricity therefrom and to also releasably retain a dental appliance and a downwardly extending bottom portion, said sleeve member being inserted into said annular cut and said bottom portion of said electrode means being placed in contact with said central opening in said stump; and
  (d) applying an electrically current to said top portion of said electrode so that said electrode conducts electricity into said stump to cause bone apposition in said stump causing bone tissue to knit through said apertures in said bottom portion of said sleeve member.

16. The method of claim 15 further comprising the step of attaching a dental appliance to said top portion of said electrode after the bone apposition has occurred.

17. The method of claim 15 wherein said forming steps further comprise shaving down the top surface of said stump to a level below the top surface of the jaw bone.

18. The method of claim 17 wherein said forming steps and said shaving step are performed simultaneously.

19. The method of claim 15 wherein said bottom portion of said electrode means is in contact with said central opening by tapping a thread in said central opening.

* * * * *